(12) United States Patent
Gavrias

(10) Patent No.: US 6,337,388 B1
(45) Date of Patent: Jan. 8, 2002

(54) ASPERGILLUS FUMIGATUS AUXOTROPHS, AUXOTROPHIC MARKERS AND POLYNUCLEOTIDES ENCODING SAME

(75) Inventor: Vicky Gavrias, Upton, MA (US)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/497,897

(22) Filed: Feb. 4, 2000

Related U.S. Application Data

(62) Division of application No. 09/040,681, filed on Mar. 18, 1998, now Pat. No. 6,090,581.
(60) Provisional application No. 60/041,300, filed on Mar. 18, 1997.

(51) Int. Cl.$^7$ .......................... C07K 1/00; C12P 21/06; C12N 1/20; C12N 15/00; C12N 1/14
(52) U.S. Cl. ................... 530/350; 435/69.1; 435/320.1; 435/252.3; 435/256.1
(58) Field of Search ....................... 530/350; 435/320.1, 435/325, 252.3, 256.1, 69.1

*Primary Examiner*—Rebecca E. Prouty
(74) *Attorney, Agent, or Firm*—Elliot M. Olstein; Alan J. Grant

(57) ABSTRACT

This invention relates to newly identified auxotrophs, polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been putatively identified as being very important to the growth and/or reproduction of *Aspergillus fumigatus*.

16 Claims, 10 Drawing Sheets

Figure 1A

```
1/1
ATG TCT CTC CCC GCA CGA ACA GCG ACC GTC TCG CGG GTG ACC AAC GAG ACC AAG ATC CAG
Met ser leu pro ala arg thr ala thr val ser arg val thr asn glu thr lys ile gln
 61/21                                   31/11
GTG TCT CTC TCT CTC GAC GGC GGC GTC CTC CCT CCA TAT GAG CCG TCA GAT CAT TTC CCT
val ser leu ser leu asp gly gly val leu pro pro tyr glu pro ser asp his phe pro
121/41                                   91/31
GCT CCT GAA GAC CCG AAG GAG GCA GCA GAG GCC AAG CAT GGC ATC GTC CCC CCC AAA AAT
ala pro glu asp pro lys glu ala ala glu ala lys his gly ile val pro pro lys asn
181/61                                  151/51
GCC GCC CAT GCG ACC CAG TTC ACA CCG ACC CAG ATC ACC GTA AGC ACG GGG ATC GGA
ala ala his ala thr gln phe thr pro thr gln ile thr val ser thr gly ile gly
241/81                                  211/71
TTT CTG GAT CAC ATG CTG CAT GCT CTC GCC AAA CAC TCT GGG TGG AGT TTA GCC ATC AGA
phe leu asp his met leu his ala leu ala lys his ser gly trp ser leu ala ile arg
301/101                                 271/91
GCC AAG GGA GAT CTG TAC ATT GAC GAC CAC CAC ACC GAA GAT ACC TTC CTT GCG CTC
ala lys gly asp leu tyr ile asp asp his his thr glu asp thr phe leu ala leu
361/121                                 331/111
GGT ACC GCC TTT ACC AAA GCT CTA GGC GCC CGG CAA TCT CTT GCA CGA TTT GGA CGC GGC
gly thr ala phe thr lys ala leu gly ala arg gln ser leu ala arg phe gly arg gly
                                        391/131
```

Figure 1B

```
421/141
GAC GCT CCA CTC GAC GAG GCT CTC TCC TGG ATC GAC CTC TCC AGC CGT CCC TGG
asp ala pro leu asp glu ala leu ser trp ile asp leu ser arg pro trp
                                        451/151
481/161
GCC GTG ATC AAC CTG GGC TTC AAG CGG GAG ATC GTG GCT GTG ACC GAG ATG ATC
ala val ile asn leu gly phe lys arg glu ile val ala val thr glu met ile
541/181                                 511/171
ACT CAT GGA CTG CAC AGC TTC GCG CAG GAT GTA ACG CTG CAT GTT GGC TGC ACA
thr his gly leu his ser phe ala gln asp val thr leu his val gly cys thr
601/201                                 571/191
TAC GGA GAT AAC GAC CAC CGT GCA GAG AGT GCG TTC AAG GCG CTG GCC GTA GCT ATC
tyr gly asp asn asp his arg ala glu ser ala phe lys ala leu ala val ala ile
661/221                                 631/211
CGC ACT GCC TGT ACC AGA AGG GTG GCT GGC GAA GTT GGA GCG GGA GAT GTG GTT AGT ACA
arg thr ala cys thr arg arg val ala gly glu val gly ala gly asp val val ser thr
721/241                                 691/231
AAG GGA GTG CTG
lys gly val leu
```

Figure 2A

```
1/1                                                                                    31/11
ATG TGG AAC TCT CCA AAG GTG GGG GTC CTC GGT GGA GGT CAG TTG GGA CGA ATG CTT GTT
Met trp asn ser pro lys val gly val leu gly gly gly gln leu gly arg met leu val
 61/21                                                     91/31
GAG TCG GCG AAC CGA CTT AAT ATC CAG GTC AAT GTT CTG GAC GCC GGT AAC GCC CCT GCG
glu ser ala asn arg leu asn ile gln val asn val leu asp ala gly asn ala pro ala
121/41                                  151/51
AAA CAA ATT AGC GCC CAC GAC GGC CAT GTG ACT GGC TCA TTC AAG GAT CGT GAA GCT GTG
lys gln ile ser ala his asp gly his val thr gly ser phe lys asp arg glu ala val
181/61                                                     211/71
CGG ACG TTG GCG AGG ACC TGC GAC GTT GTG ACG GCC GAG ATC GAG CAT GTT GAT ACA TAC
arg thr leu ala arg thr cys asp val val thr ala glu ile glu his val asp thr tyr
241/81                                  271/91
GCT CTT GAG GAG ATC TCC GCG ATC GAG GTC AAG GTT GAG CCC AGC TGG CAA GCG ATC CGA ACA
ala leu glu glu ile ser ala glu val lys val glu pro ser trp gln ala ile arg thr
301/101                                                    331/111
ATC CAG AAC AAG TTC AAT CAG AAG GAA CAC CTT CGG AAA TAT GGC ATA CCA ATG GCG GAG
ile gln asn lys phe asn gln lys glu his leu arg lys tyr gly ile pro met ala glu
361/121                                 391/131
CAC CGG GAG CTG CTT GAG AAC ACG CCG GCT GAA CTC GCC CAG ATC GGC GAA CAG CTT GGG
his arg glu leu leu glu asn thr pro ala glu leu ala gln ile gly glu gln leu gly
```

Figure 2B

```
421/141
TAT CCC TTG ATG CTC AAG ACG ATG GCC TAC GAC GGA CGG GGA AAC TTC CGT GTC
tyr pro leu met leu lys thr met ala tyr asp gly arg gly asn phe arg val
481/161                              451/151
AAT TCC AAG GAC GAT ATC CCC GAA GCG CTC GAA GCG CTC AAG GAC CGG CCA TTG TAC GCT
asn ser lys asp asp ile pro glu ala leu glu ala leu lys asp arg pro leu tyr ala
541/181
GAG AAA TGG GCC TAC TTC AAG ATG GAA TTG GCC GTA ATG GTT GTG AAA ACC AAG GAC GCG
glu lys trp ala tyr phe lys met glu leu ala val met val lys thr lys asp ala
601/201
GTC CTC TCA TAC CCC ACA GTC GAG ACA GTA CAA GAA GAT TCG ATA TGC AAG CTC GTC TAC
val leu ser tyr pro thr val glu thr val gln glu asp ser ile cys lys leu val tyr
661/221
GCA CCT GCC CGC AAT GTC TCC GAC GCC ATC AAC CAG AAA GCC CAG GAG CTA GCC CGC AAG
ala pro ala arg asn val ser asp ala ile asn gln lys ala gln glu leu ala arg lys
721/241
GCT GTC GCA GCC TTT GAC GGC AAG GGT GCT TTC GGT GTG GAG ATG TTC CTT CTC GAG GAC
ala val ala ala phe asp gly lys gly ala phe gly val glu met phe leu leu glu asp
781/261                                                                 811/271
GAC AGC ATC ATG CTG TGC GAA ATT GCC AGC CGC ATC CAC AAC TCG GCC CAC TAC ACA ATT
asp ser ile met leu cys glu ile ala ser arg ile his asn ser gly his tyr thr ile
```

Figure 2C

```
841/281
GAA GGT TGT ACC CTG TCC CAA TTT GAC GCC CAC CTA CGT GCC ATT CTC GAC CTC CCC ATT
glu gly cys thr leu ser gln phe asp ala his leu arg ala ile leu asp leu pro ile
901/301                                                 871/291
CCC CCT CAG AGC CTC GAA ATC CGC CAA CCG TCC ATC ATG CTC AAC ATC ATT GGC GGC GCC
pro pro gln ser leu glu ile arg gln pro ser ile met leu asn ile ile gly gly ala
961/321                                     931/311
GCC CCA GAC ACC CAC CTG AAA GCC GCC GAG GCT CTC TCC ATC CCC AAC GCC AGC ATT
ala pro asp thr his leu lys ala ala glu ala leu ser ile pro asn ala ser ile
1021/341                                    991/331
CAC CTC TAC AGC AAG GGC GCC GCC AAG CCC GGC CGC AAG ATG GGC CAC GTC ACC GTT ACC
his leu tyr ser lys gly ala ala lys pro gly arg lys met gly his val thr val thr
1081/361                                    1051/351
GCG TCC ACG ATG CAC GAA GCC GAG AAA TAC ATC CAG CCC CTG ATC GAC GTT GTT GAC GAG
ala ser thr met his glu ala glu lys tyr ile gln pro leu ile asp val val asp glu
1141/381                                    1111/371
ATC CGC TCG AAG CGC AGC GAC ATC AAG ACA CAG CCC GTC AAG TCC GGC CCG TCG AAG CCC
ile arg ser lys arg ser asp ile lys thr gln pro val lys ser gly pro ser lys pro
1201/401                                    1171/391
GCC CCC ACC GTT GCT GTG ATG ATG GGC TCC GAT AGC GAC CTC AAG ACA CTC GTT CCG GGC
ala pro thr val ala val met met gly ser asp ser asp leu lys thr leu val pro gly
                                            1231/411
```

Figure 2D

```
1261/421                                                      1291/431
CTG AAA CTC CTC CGT GAC TAC TTC GGC ATC GAG CCC GCC GTC GAC ATC ACC TCC GCC CAT
leu lys leu leu arg asp tyr phe gly ile glu pro ala val asp ile thr ser ala his
1321/441                                              1351/451

CGC ACC CCA ACG TTC ATG GCC GAG TAC TCA AGC GCA GCC GCG CGC GGC ATT AAG GTC
arg thr pro thr phe met ala glu tyr ser ala ala arg gly ile lys val
1381/461                                      1411/471

ATT ATC GCC GCT GGC GGC GGC GCC CAT CTC CCT GGG ATG GCT GCC GCA CAC ACC GTC
ile ile ala ala gly gly gly ala his leu pro gly met ala ala ala his thr val
1441/481                                      1471/491

CTG CCC GTC ATC GGC GTA CCG GTC AAG GGC TCG CTA GAC GGC GTG GAC AGC CTG TAC
leu pro val ile gly val pro val lys gly ser ser leu asp gly val asp ser leu tyr
1501/501                                      1531/511

AGC ATC GTC CAG ATG CCT AGA GGT GTT CCC GCG ACG GTA GGA ATC AAC AAC AGC ATC
ser ile val gln met pro arg gly val pro ala thr val gly ile asn asn ser ile
1561/521                                      1591/531

AAC GCT GCC CTC CTG GCA GCT CGT ATC CTT GGC ACA TTC GAC CCG GCT ATC CAG CGT AAG
asn ala ala leu leu ala ala arg ile leu gly thr phe asp pro ala ile gln arg lys
1621/541                                      1651/551

GTG GAG GCG TAT GCC GAG CAG GCT AGA CAC GAG AAC ATG GAG TTG AAG GGG ACC AAG ATG
val glu ala tyr ala glu gln ala arg his ala arg his glu asn met glu leu lys gly thr lys met
1681/561                                      1711/571

CAG GAA CTC GGA TGG GAA AAG TAC TTT GAA CAG ATG
gln glu leu gly trp glu lys tyr phe glu gln met
```

Figure 3A

```
1/1
ATG CCG TCA TAT AAC ATT GTC GTT TTC GCT GGG GAC CAC TGT GGT CCG GAG GTG ACC GCT
Met pro ser tyr asn ile val val phe ala gly asp his cys gly pro glu val thr ala
                                    31/11
61/21
GAG GCA ATC AAG GTC CTG CGC GTC ATC GAG ATC AAG TGC CGT GAC GAT GCT ACC TTC AAC CTC
glu ala ile lys val leu arg val ile glu ile lys cys arg asp asp ala thr phe asn leu
                                    91/31
121/41                              151/51
CAG GAT CAA TTG CTC GGT GGT GCA TCG ATC GAT GCT ACC GGA TCT CCC CTT ACC GAC GAA
gln asp gln leu leu gly gly ala ser ile asp ala thr gly ser pro leu thr asp glu
181/61                              211/71
GCT CTT AAC GCC GCA AAG AAC GCC GAT GCC GTT CTC CTC CGT CTG GCC ATT GGC GGT CCC AAA
ala leu asn ala ala lys asn ala asp ala val leu leu gly leu ala ile gly gly pro lys
241/81                              271/91
TGG GGC ACT GGC GCC GTC CGC CCC GAA CAG GGC CTC CTC CGT CTG CGC AAG GAG ATG GGC
trp gly thr gly ala val arg pro glu gln gly leu leu arg leu arg lys glu met gly
301/101                             331/111
ACA TTC GGT AAC CTC CGC CCC TGC AAC TTC GCC GCC CCG TCG CTG GTC GAC GGC TCC CCT
thr phe gly asn leu arg pro cys asn phe ala ala pro ser leu val asp gly ser pro
```

Figure 3B

```
361/121
CTC CGC CCC GAA GTC TGC CGC GGC GTC GAC ATT ATC CGC GAA CTG ACC GGT GGC
leu arg pro glu val cys arg gly val asp ile ile arg glu leu thr gly gly
421/141                                391/131
ATC TAC TTC GGC GAC CGC AAG GAG GAC GAC AGC GGC TTC GCC ATG GAC ACG GAG CCG
ile tyr phe gly asp arg lys glu asp asp ser gly phe ala met asp thr glu pro
481/161                                451/151
TAC TCC CGC GCG GAG ATC GAG CGC ATC ACC CGC CTT GCG GCC CAC CTC CTG CAG CAC
tyr ser arg ala glu ile glu arg ile thr arg leu ala ala his leu leu gln his
541/181                                511/171
AAC CCC CCT CTT CCC GTG TGG AGC TTG GAC GCC AAG GCC AAC GTC CTC GCG AGC CGG CTG
asn pro pro leu pro val trp ser leu asp ala lys ala asn val leu ala thr ser arg leu
601/201                                571/191
TGG CGG AAG ACC GTG ACG GAG GTC ATG GCC AAG GAG TTC CCC CAG CTC AAG GTG GAG CAC
trp arg lys thr val thr glu val met ala lys glu phe pro gln leu lys val glu his
661/221                                631/211
CAG CTC ATT GAC TCC GCG GCC ATG ATC ATG GTC AAG GAG CCT AGA AAG CTT AAC GGT ATT
gln leu ile asp ser ala ala met ile met val lys glu pro arg lys leu asn gly ile
                                       691/231
```

Figure 3C

```
721/241
GTT GTC ACT AGC AAC CTG TTC GGT GAC ATC AGT GAT GAA GCC AGC GTT ATC CCT GGT
val val thr ser asn leu phe gly asp ile ser asp glu ala ser val ile pro gly
781/261                                            751/251
TCT CTG GGA CTC TTG CCC AGC GCA AGC TTG AGC GGC ATT CCT GAC GGA AAG ACC AAG GTC
ser leu gly leu leu pro ser ala ser leu ser gly ile pro asp gly lys thr lys val
841/281                                            811/271
AAT GGT ATC TAT GAG CCT ATT CAC GGT TCT GCC CCT GAC ATT GCC GGC AAG GGC ATC GTT
asn gly ile tyr glu pro ile his gly ser ala pro asp ile ala gly lys gly ile val
901/301                                            871/291
AAC CCC GTC GCC GCC ATT CTC TCT GTC GCC ATG ATG CAG TAC TCC CTG AAC CGT ATG
asn pro val ala ala ile leu ser val ala met met gln tyr ser leu asn arg met
961/321                                            931/311
GAT GAC GCC AGG GCC ATC GAG ACG GCC GTC AAT GTG CGC AAT GTG ATC GAG GCC GGT ATC CGC ACT
asp asp ala arg ala ile glu thr ala val asn val arg asn val ile glu ala gly ile arg thr
1021/341                                           991/331
GCC GAT ATT GGC GGC AAG TCG ACA ACT AGC GAG GTC GGT GAC GCT GTT GCT GCC GAG CTG
ala asp ile gly gly lys ser thr thr ser glu val gly asp ala val ala ala glu leu
1081/361                                           1051/351
GAG AAG CTG TTG AAG CAA
glu lys leu leu lys gln
```

IMIDAZOLEGLYCEROL-P DEHYDRATASE

*A. fumifatus hisB* Knockout Construction

ASPERGILLUS FUMIGATUS AUXOTROPHS, AUXOTROPHIC MARKERS AND POLYNUCLEOTIDES ENCODING SAME

This application is a divisional of U.S. application No. 09/040,681, filed Mar. 18, 1998, now U.S. Pat. 6,090,581, issued Jul. 18, 2000, which claims the benefit of U.S. Provisional application No. 60/041,300, filed Mar. 18, 1997.

BACKGROUND OF THE INVENTION

This invention relates to newly identified auxotrophs, polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been putatively identified as being very important to the growth and/or reproduction of *Aspergillus fumigatus*.

Generally, such proteins are of such importance to the growth and/or reproduction of *Aspergillus fumigatus* that modifications to the protein or to the polynucleotide encoding same, blocking the expression or activity of the protein, or deleting or disabling the polynucleotide encoding the protein will have a significant and clearly observable effect on either the growth or reproduction of the organism in vitro. In fact, absent a supplemented media having a particular substance that would have resulted from the synthesis pathway in which the protein functions, the *Aspergillus fumigatus* auxotrophs will die.

In accordance with one aspect of the present invention there are provided auxotrophic microbes of the *Aspergillus fumigatus* type, which are incapable of growth and reproduction in vitro in the absence of a media supplemented by at least one chemical compound that is not required for a non-auxotrophic microbe of the *Aspergillus fumigatus* type.

In accordance with another aspect of the present invention, there are provided novel proteins, as well as active fragments, analogs and derivatives thereof.

In accordance with another aspect of the present invention, there are provided isolated nucleic acid molecules encoding the proteins of the present invention including mRNAs, cDNAs, genomic DNAs as well as active analogs and fragments of such proteins.

In accordance with another aspect of the present invention there are provided strains of auxotrophic *Aspergillus fumigatus* microbe which have the ATCC Deposit Nos. AFH153 209347, AFLEU2 209348, and AFADE2 209349.

In accordance with another aspect of the present invention there are provided isolated nucleic acid molecules encoding mature polypeptides expressed by the DNA contained in ATCC Deposit Nos. AFH153 209347, AFLEU2 209348, and AFADE2 209349.

In accordance with yet a further aspect of the present invention, there is provided a process for producing such polypeptides by recombinant techniques comprising culturing recombinant prokaryotic and/or eukaryotic host cells, containing a nucleic acid sequence of the present invention, under conditions promoting expression of said proteins and subsequent recovery of said proteins.

In accordance with yet a further aspect of the present invention, there is provided a process for utilizing such proteins to produce antibodies specific for such proteins to permit analyzing a vector or host cell for the presence of the protein, which is heterologous to said vector or host cell. Thus, the protein is useful as a heterologous marker wherein the polynucleotide sequence encoding the protein is part of a construct inserted into a vector or host wherein such protein would be heterologous.

In accordance with a still further aspect of the invention another process utilizes the polynucleotides to assay for compounds which bind said polynucleotides and would thus block expression of any products from said polynucleotides.

In another aspect polynucleotides of the invention may be employed as a tool for studying *Aspergillus fumigatus* to ascertain various genes thereof, particularly other essential genes. One such process is useful for analyzing for the functionality of an unknown function cDNA from an *Aspergillus fumigatus* cDNA library comprising obtaining an auxotrophic strain of *Aspergillus fumigatus*, obtaining a polynucleotide construct comprising (i) a polynucleotide sequence capable of removing the auxotrophic property and (ii) at least one portion of the unknown function cDNA polynucleotide sequence. which is not the complete cDNA sequence from the cDNA library, and inserting said construct into said auxotrophic strain. Preferably, such a process involves an auxotroph that requires either histidine, adenylic acid, or leucine to grow and reproduce. A further preferred process, comprises assaying the auxotrophic strain for growth and reproduction in a media which lacks, histidine, adenylic acid, or leucine to confirm insertion of the construct. An ever further preferred process also comprises assaying the strain with the insertion for a lost property, which would have resulted from the unknown cDNA corresponding to the cDNA of the cDNA library.

*Aspergillus fumigatus* are microbes which are useful as host cells for the expression of heterologous polynucleotide sequences and for production of heterologous proteins. It would be helpful in such an environment to map more or all of the genes in This microbe in order to enhance its use as a host cell for expression of heterologous polynucleotide sequences and for production of heterologous proteins. Auxotrophs are useful in that they need a specific supplement in their media or they don't grow or reproduce, and in fact may die. Thus, advantageously, a construct is made which comprises either the head or tail portion (preferably at least 250 base pairs in length) of the polynucleotide sequence that will cure (remove) the auxotrophic property ligated to the heterologous gene which is in turn ligated to the full polynucleotide sequence which will remove the auxotrophic property. Preferably, the construct may comprise a promoter sequence or a secretion coding sequence for the heterologous gene. Therefore, if a heterologous polynucleotide construct is inserted into the auxotroph which includes the gene encoding a protein or polypeptide (preferably according to this invention) which will eliminate the need for the supplement in the media, the auxotrophs can be conveniently screened for the successful insertion of the construct.

After attempts to insert the construct by homologous recombination (cross-over) in the auxotroph, the potential transformants are plated on supplemented media to culture colonies from a single isolated cell. Cells from a particular colony can then be plated on a media which lacks the supplement required by the starting auxotroph, species where insertion has been successful will grow on the media lacking that supplement, but species lacking the insert will fail to grow or reproduce and in fact may die. Accordingly, auxotrophs are useful tools to screen for successful insertion of heterologous genes which are part of a construct that removes the auxotrophic property of the auxotroph.

Such auxotrophs and the polynucleotides which encode for a protein which will remove a particular auxotrophic property of the auxotroph are also useful tools in the study of the genus or species of microbe from which the auxotroph is obtained. A vector containing a cDNA of unknown function from a cDNA library for the microbe may be utilized to form a construct having only a portion of the cDNA and including the known polynucleotide encoding the known protein which will eliminate the auxotrophic property of the auxotroph. The active gene corresponding to the cDNA from the library is disabled by successful insertion of the construct. For example, the culture is screened for successful insertion of the construct as discussed above, in a media which is fully supplemented except for the supplement required by the starting auxotroph. Species having the successful insertion, may then be studied to obtain the property of the disabled gene corresponding to the cDNA. For example, supplements may be individually omitted from the growth media until an effect is observed such as diminished growth or death, and the area of functionally of the gene corresponding to the cDNA is thus identified.

Accordingly, a process to determine the function of unknown genes within *Aspergillus fumigatus* utilizing the polynucleotides and/or proteins of the present invention is also an important and useful procedure made possible by the present invention.

There are other applications for the proteins and polynucleotides of the present invention in various industries which may utilize such microbe, such as in the fermentation industry. Since such proteins and/or polynucleotides have been found to be significantly essential to the growth and/or reproduction of *Aspergillus fumigatus* they may be useful to determine agonist which may enhance the growth and/or reproduction of such microbe in such fermentation processes. Moreover, the expression products of the polynucleotides according to the invention may be useful to enhance the growth of such microbe, e.g., multiple copies of the present gene in *Aspergillus fumigatus* may prove to enhance its growth or reproductive rates.

In accordance with yet a further aspect of the present invention, there are also provided nucleic acid probes comprising nucleic acid molecules of sufficient length to specifically hybridize to a nucleic acid sequence of the present invention.

In accordance with yet a further aspect of the present invention, there is provided a process for utilizing such proteins, or polynucleotides encoding such proteins, for purposes related to scientific research, for example, to generate probes for identifying similar sequences which might encode similar proteins from other organisms by using certain regions, i.e., conserved sequence regions, of the nucleotide sequence.

These and other aspects of the present invention should be apparent to those skilled in the art from the teachings herein.

BRIEF DESCRIPTION OF THE DRAWINGS

The following drawings are illustrative of an embodiment of the invention and are not meant to limit the scope of the invention as encompassed by the claims.

FIG. 1 illustrates a nucleotide sequence from a *Aspergillus fumigatus* cDNA (SEQ ID NO:1) encoding and the deduced amino acid sequence (SEQ ID NO:2) therefor. The omission of such polynucleotide from *Aspergillus fumigatus* results in an auxotrophic species that require a growth media supplemented with the amino acid histidine. The top line of each set of rows is the polynucleotide sequence, the second line contains the threeletter codes representing the deduced amino acid sequence encoded by the polynucleotide.

FIG. 2 illustrates a nucleotide sequence from a *Aspergillus fumigatus* cDNA (SEQ ID NO:3) encoding and the deduced amino acid sequence (SEQ ID NO:4) therefor. The omission of such polynucleotide from *Aspergillus fumigatus* results in an auxotrophic species that require a growth media supplemented with adenylic acid. The top line of each set of rows is the polynucleotide sequence, the second line contains the three-letter codes representing the deduced amino acid sequence encoded by the polynucleotide.

FIG. 3 illustrates a nucleotide sequence from a *Aspergillus fumigatus* cDNA (SEQ ID NO:5) encoding and the deduced amino acid sequence (SEQ ID NO:6) therefor. The omission of such polynucleotide from *Aspergillus fumigatus* results in an auxotrophic species that require a growth media supplemented with the amino acid leucine. The top line of each set of rows is the polynucleotide sequence, the second line contains the three-letter codes representing the deduced amino acid sequence encoded by the polynucleotide.

Figure 4:
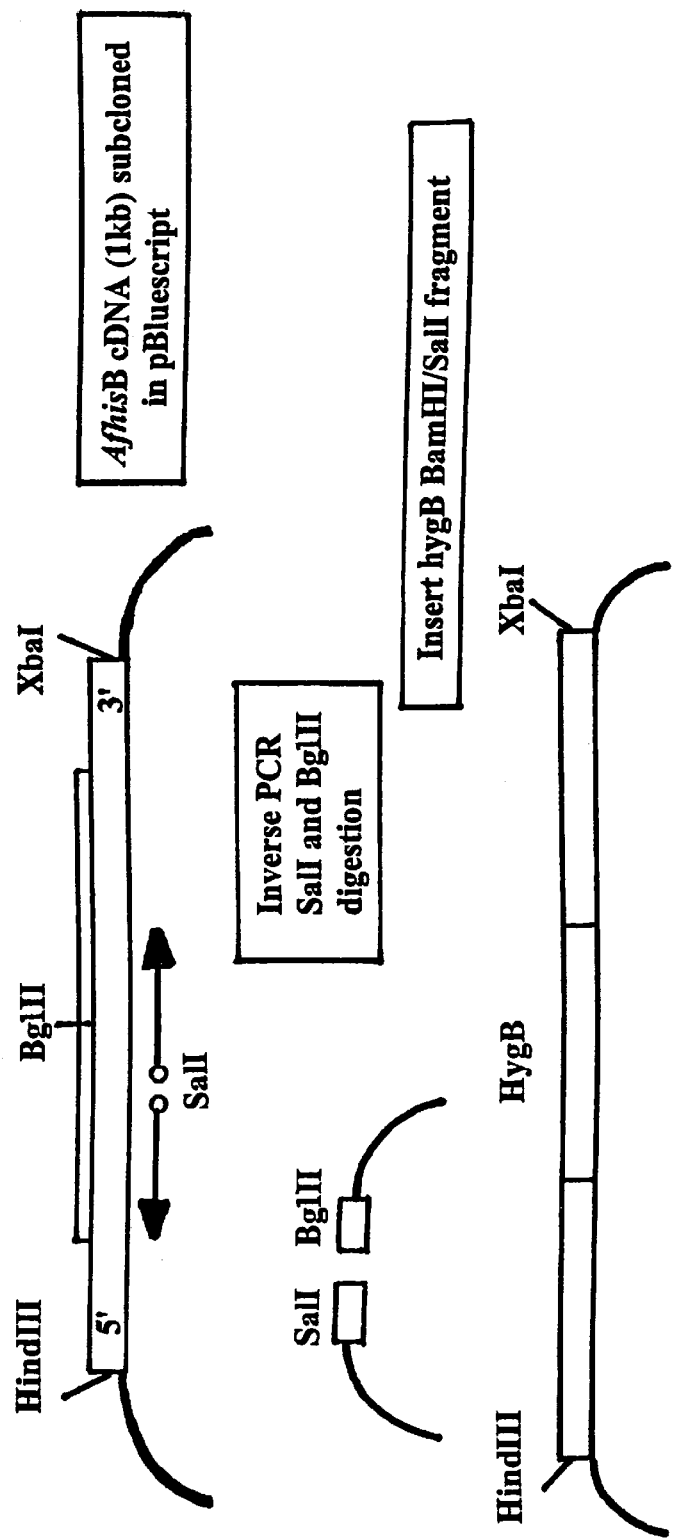
FIG. 4 illustrates the structure of a hisB knockout construct which may be utilized to produce an auxotroph which requires a medium supplemented with the amino acid histidine. In this illustration a construct is made which corresponds to the portions of the head and tail of the polynucleotide according to nucleotide sequence SEQ ID NO:1 from *Aspergillus fumigatus* having sandwiched in between a gene for hygB. An hygB insert having a BamHI/SaII fragment is shown. Inverse digestion is utilized to cut out the middle portion of the polynucleotide according to SEQ ID NO:1 and the hygB fragment is inserted to form the construct.

*Aspergillus fumigatus* was transformed with the construct described in FIG. 4 to permit cross-over replacement of the gene corresponding to SEQ ID NO:1 with the construct in a medium supplemented with amino acid histidine. In such cross-over replacement the construct substitutes itself for the polynucleotide sequence according to SEQ ID NO:1 which is then eliminated by the cell. The cells were screened using screening procedures to assay members of pure colonies for the auxotrophic property of requiring a medium supplemented by the amino acid histidine. Of 1 75 colonies of potential transformants screened in a medium lacking the amino acid histidine, 20 transformant species were identified as auxotrophs of *Aspergillus fumigatus* that require histidine for growth.

DEFINITIONS

In order to facilitate understanding of the following description and examples which follow certain frequently occurring methods and/or terms will be described.

The term "auxotroph" refers to a species of a cell type, whether naturally occurring or is produced by other means which requires at least one supplement in its growth media in order to grow and reproduce, as contrasted to a species which does not require such a supplement for growth and reproduction.

The term "construct" refers to a polynucleotide segment adapted to insertion into a longer polynucleotide via a ligation procedure or by crossover replacement of a portion of the longer chain polynucleotide.

The term "cross-over replacement" refers to the replacement of a portion of a polynucleotide chain with a construct by alignment of the construct with a portion of a polynucleotide chain in a cell such that the portion is replaced with the construct and the original polynucleotide portion is eliminated. Such cross-over replacement is most likely to occur during a reproduction phase of the cell.

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

"Recombinant" proteins refer to proteins produced by recombinant DNA techniques; i.e., produced from cells transformed by an exogenous DNA construct encoding the desired protein. "Synthetic" proteins are those prepared by chemical synthesis.

A DNA "coding sequence of" or a "nucleotide sequence encoding" a particular protein, is a DNA sequence which is transcribed and translated into a protein when placed under the control of appropriate regulatory sequences.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel et al., *Nucleic Acids* Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., *Id.*, p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in Sambrook and Maniatis, Molecular Cloning: A Laboratory Manual, Cold Spring Harbor Laboratory, 1989.

SUMMARY OF THE INVENTION

In accordance with an aspect of the invention there are provided auxotrophic microbes of the *Aspergillus fumigatus* type, which either lack or have disabled one or more of the genes corresponding to a polynucleotide sequence selected from SEQ ID NO:1, 3, or 5, respectively, requiring histidine, adenylic acid, or leucine for growth and reproduction. The deposited auxotrophs are deposited with the American Type Culture Collection, 10801 University Blvd., Manassas, Va. 20110-2209, USA, the deposited materials are assigned ATCC Deposit Nos. AFH153 209347, AFLEU2 209348, and AFADE2 209349 (corresponding to FIGS. 1–3, respectively).

In accordance with an aspect of the present invention, there are provided isolated nucleic acids (polynucleotides) from *Aspergillus fumigatus* (SEQ ID NOS: 1, 3 and 5) which encode the mature protein having the continuous deduced amino acid sequence shown in FIGS. 1–3, respectively (SEQ ID NOS:2, 4 and 6, respectively).

In accordance with another aspect of the present invention, there is provided isolated polynucleotides encoding the proteins of the present invention. The deposited material is a genomic clone comprising DNA encoding a protein of the present invention, in a plasmid DNA vector form. As deposited with the American Type Culture Collection, 10801 University Blvd., Manassas, Va. 20110-2209, USA, the deposited materials are assigned ATCC Deposit Nos. AFH153 209347, AFLEU2 209348, and AFADE2 209349 (corresponding to FIGS. 1–3, respectively).

The deposits have been made under the terms of the Budapest Treaty on the International Recognition of the Deposit of Micro-organisms for Purposes of Patent Procedure. The clones will be irrevocably (without restriction or condition except as permitted for enforcement of a patent) released to the public upon the issuance of a patent. The deposits are provided merely as a convenience to those of skill in the art and is not an admission that any deposit would be required under 35 U.S.C. §112. The sequence of the polynucleotide contained in the respective deposited materials, as well as the amino acid sequences of the polypeptide encoded thereby, are controlling in the event of any conflict with any description of sequences herein. A license may be required to make, use or sell the deposited material, and no such license is hereby granted.

DETAILED DESCRIPTION OF THE INVENTION

The polynucleotides of this invention coding for the proteins of this invention were originally recovered from a genomic gene library derived from *Aspergillus fumigatus*.

One means for isolating the nucleic acid molecules encoding the proteins of the present invention is to probe a *Aspergillus fumigatus* gene library with a natural or artificially designed probe using art recognized procedures (see, for example: Current Protocols in Molecular Biology, Ausubel F. M. et aL (EDS.) Green Publishing Company Assoc. and John Wiley lnterscience, New York, 1989, 1992). It is appreciated by one skilled in the art that the polynucleotides of SEQ ID NOS:1, 3 and 5, or fragments thereof (comprising at least 12 contiguous nucleotides), are particularly useful probes. Other particularly useful probes for this purpose are hybridizable fragments of the sequences of SEQ ID NOS:1, 3 and 5 (i.e., comprising at least 12 contiguous nucleotides).

With respect to nucleic acid sequences which hybridize to specific nucleic acid sequences disclosed herein, hybridization may be carried out under conditions of reduced stringency, medium stringency or even stringent conditions.

As an example of oligonucleotide hybridization, a polymer membrane containing immobilized denatured nucleic acids is first prehybridized for 30 minutes at 45° C. in a solution consisting of 0.9 M NaCl, 50 mM NaH$_2$PO$_4$, pH 7.0, 5.0 mM Na$_2$EDTA, 0.5% SDS, 10×Denhardt's, and 0.5 mg/mL polyriboadenylic acid. Approximately 2×10$^7$ cpm (specific activity 4–9×10$^8$ cpm/ug) of $^{32}$p end-labeled oligonucleotide probe are then added to the solution. After 12–16 hours of incubation, the membrane is washed for 30 minutes at room temperature in 1×SET (150 mM NaCl, 20 mM Tris hydrochloride, pH 7.8, 1 mM Na$_2$EDTA) containing 0.5% SDS, followed by a 30 minute wash in fresh 1×SET at Tm less 10° C. for the oligonucleotide probe. The membrane is then exposed to auto-radiographic film for detection of hybridization signals.

Stringent conditions means hybridization will occur only if there is at least 90% identity, preferably at least 95% identity and most preferably at least 97% identity between the sequences. Further, it is understood that a section of a 100 bps sequence that is 95 bps in length has 95% identity with the 1090 bps sequence from which it is obtained. See J. Sambrook et al., *Molecular Cloning, A Laboratory Manual*, 2d Ed., Cold Spring Harbor Laboratory (1989) which is hereby incorporated by reference in its entirety. Also, it is understood that a fragment of a 100 bps sequence that is 95 bps in length has 95% identity with the 100 bps sequence from which it is obtained.

As used herein, a first DNA (RNA) sequence is at least 70% and preferably at least 80% identical to another DNA (RNA) sequence if there is at least 70% and preferably at least a 80% or 90% identity, respectively, between the bases of the first sequence and the bases of the another sequence, when properly aligned with each other, for example when aligned by BLASTN.

The present invention relates to polynucleotides which differ from the reference polynucleotide in a manner such that the change or changes is/are silent change, in that the amino acid sequence encoded by the polynucleotide remains the same. The present invention also relates to nucleotide changes which result in amino acid substitutions, additions, deletions, fusions and truncations in the polypeptide encoded by the reference polynucleotide. In a preferred aspect of the invention these polypeptides retain the same biological action as the polypeptide encoded by the reference polynucleotide.

The polynucleotides of the present invention may be in the form of RNA or DNA which DNA includes cDNA, genomic DNA, and synthetic DNA. The DNA may be double-stranded or single-stranded, and if single stranded may be the coding strand or non-coding (anti-sense) strand. The coding sequences which encodes the mature proteins may be identical to the coding sequences shown in FIGS. 1–3, (SEQ ID NOS:1, 3 and 5, respectively) or may be a different coding sequence which coding sequence, as a result of the redundancy or degeneracy of the genetic code, encodes the same mature proteins as does the DNA of FIGS. 1–3, (SEQ ID NOS:1, 3 and 5, respectively).

The polynucleotides which encode each of the mature proteins (SEQ ID NOS:2, 4 and 6, respectively) may include, but each is not limited to: only the coding sequence for the mature protein; the coding sequence for the mature protein and additional coding sequence such as a leader sequence or a proprotein sequence; the coding sequence for the mature protein (and optionally additional coding sequence) and non-coding sequence, such as introns or non-coding sequence 5' and/or 3' of the coding sequence for the mature protein.

Thus, the term "polynucleotide encoding a protein" encompasses a polynucleotide which includes only coding sequence for the protein as well as a polynucleotide which includes additional coding and/or non-coding sequences.

The present invention further relates to variants of the hereinabove described polynucleotides which encode for fragments, analogs and derivatives of the proteins having the deduced amino acid sequences of FIGS. 1–3 (SEQ ID NOS: 2, 4 and 6, respectively). The variant of the polynucleotide may be a naturally occurring allelic variant of the polynucleotide or a non-naturally occurring variant of the polynucleotide.

Thus, the present invention includes polynucleotides encoding the same mature proteins as shown in FIGS. 1–3 as well as variants of such polynucleotides which variants encode for a fragment, derivative or analog of the proteins of FIGS. 1–3 respectively. Such nucleotide variants include deletion variants, substitution variants and addition or insertion variants.

As hereinabove indicated, the polynucleotides may have a coding sequence which is a naturally occurring allelic variant of the coding sequence shown in FIGS. 1–3 As known in the art, an allelic variant is an alternate form of a polynucleotide sequence which may have a substitution, deletion or addition of one or more nucleotides, which does not substantially alter the function of the encoded protein. Also, using directed and other evolution strategies, one may make very minor changes in DNA sequence which can result in major changes in function.

Fragments of the full length gene of the present invention may be used as hybridization probes for a cDNA or a genomic library to isolate the full length DNA and to isolate other DNAs which have a high sequence identity to the gene. Probes of this type preferably have at least 10, preferably at least 15, and even more preferably at least 30 bases and may contain, for example, at least 50 or more bases. In fact, probes of this type having at least up to 150 bases or greater may be utilized. The probe may also be used to identify a DNA clone corresponding to a full length transcript and a genomic clone or clones that contain the complete gene including regulatory and promotor regions, exons and introns. An example of a screen comprises isolating the coding region of the gene by using the known DNA sequence to synthesize an oligonucleotide probe. Labeled oligonucleotides, having a sequence complementary to that of the gene or portion of the gene sequences of the present invention are used to screen a library of genomic DNA to determine which members of the library the probe hybridizes to in a complementary sense, have an identity as described above.

It is also appreciated that such probes can be and are preferably labeled with an analytically detectable reagent to facilitate identification of the probe. Useful reagents include but are not limited to radioactivity, fluorescent dyes or proteins capable of catalyzing the formation of a detectable product. The probes are thus useful to isolate complementary copies of DNA from other sources or to screen such sources for related sequences.

The present invention further relates to polynucleotides which hybridize to the hereinabove-described sequences if there is at least 70%, preferably at least 90%, and more preferably at least 95% identity between the sequences. (As indicated above, 70% identity would include within such definition a 70 bps fragment taken from a 100 bp polynucleotide, for example.) The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode proteins which either retain substantially the same biological function or activity as the mature proteins encoded by the DNA of FIGS. 1–3 respectively. In referring to identity in the case of hybridization, as known in the art, such identity refers to complementarity of polynucleotide segments.

Alternatively, the polynucleotide may have at least 15 bases, preferably at least 30 bases, and more preferably at least 50 bases which hybridize to any part of a polynucleotide of the present invention and which has an identity thereto, as hereinabove described, and which may or may not retain activity. For example, such polynucleotides may be employed as probes for the polynucleotides of SEQ ID NOS: 1, 3 and 5, for example, for recovery of the polynucleotide or as a diagnostic probe or as a PCR primer.

Thus, the present invention is directed to polynucleotides having at least a 70% identity, preferably at least 90% identity and more preferably at least a 95% identity to a polynucleotide which encodes the polypeptides of SEQ ID NOS: 2, 4 and 6, respectively, as well as fragments thereof, which fragments have at least 15 bases, preferably at least 30 bases, more preferably at least 50 bases and most preferably fragments having up to at least 150 bases or greater, which fragments are at least 90% identical, preferably at least 95% identical and most preferably at least 97% identical to any portion of a polynucleotide of the present invention.

The present invention further relates to proteins which have the deduced amino acid sequence of FIGS. 1–3 respectively, (SEQ ID NOS: 2, 4 and 6, respectively) as well as fragments, analogs and derivatives of such proteins.

The terms "fragment," "derivative" and "analog" when referring to each of the proteins of FIGS. 1–3 respectively, (SEQ ID NO: 2, 4 and 6, respectively) generally mean a protein which retains essentially the same biological function or activity as such protein. Thus, an analog includes a proprotein which can be activated by cleavage of the proprotein portion to produce an active mature protein.

The proteins of the present invention may be a recombinant protein, a natural protein or a synthetic protein, preferably a recombinant protein.

The present invention further relates to polypeptides encoded by polynucleotides which have at least 70%, preferably at least 90%, and more preferably at least 95% identity between their polynucleotide sequence and one of the sequences according to SEQ ID NO:1, 3 or 5, respectively. (As indicated above, 70% identity would include within such definition a 70 bps fragment taken from a 100 bp polynucleotide, for example.) The present invention particularly relates to polypeptides encoded by polynucleotides which hybridize under stringent conditions to the hereinabove-described polynucleotides or their complement. As herein used, the term "stringent conditions" means hybridization will occur only if there is at least 95% and preferably at least 97% identity between the sequences. The polynucleotides which hybridize to the hereinabove described polynucleotides in a preferred embodiment encode proteins which either retain substantially the same biological function or activity as the mature proteins encoded by the DNA of FIGS. 1–3 respectively. However, polypeptides having at least 70% or greater identity as described above are useful marker proteins in their own right regardless of whether the possess the biological activity of one of the polypeptides having an amino acid sequence according to SEQ ID NO:2, 4, or 6, respectively. Such are useful in a process to produce antibodies specific for such polypeptides to permit analyzing a vector or host cell for the presence of the polypeptide, which is heterologous to that vector or host cell. Thus, the polypeptide is useful as a heterologous marker wherein the polynucleotide sequence encoding the polypeptide is part of a construct inserted into a vector or host wherein such polypeptide would be heterologous. Pure cultures of the vector or host cell could be assayed for expression of the heterologous polypeptide to indicate a successful insertion of the construct which comprised the polynucleotide sequence encoding the heterologous polypeptide. In referring to identity in the case of hybridization, as known in the art, such identity refers to complementarity of polynucleotide segments.

The fragment, derivative or analog of each of the proteins of FIGS. 1–3 respectively, (SEQ ID NOS: 2, 4 and 6, respectively) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature protein is fused with another compound, such as a compound to increase the half-life of the protein (for example, polyethylene glycol), or (iv) one in which the additional amino acids are fused to the mature protein, such as a leader or secretory sequence or a sequence which is employed for purification of the mature protein or a proprotein sequence. Such fragments, derivatives and analogs are deemed to be within the scope of those skilled in the art from the teachings herein.

The proteins and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or protein present in a living animal is not isolated, but the same polynucleotide or protein, separated from some or all of the coexisting materials in the natural system, is isolated. Such polynucleotides could be part of a vector and/or such polynucleotides or proteins could be part of a composition, and still be isolated in that such vector or composition is not part of its natural environment.

The proteins of the present invention include the respective proteins of SEQ ID NOS: 2, 4 and 6, (in particular the mature proteins) as well as proteins which have at least 70% similarity (preferably at least 70% identity) to the respective proteins of SEQ ID NOS: 2, 4 and 6 and more preferably at least 90% similarity (more preferably at least 90% identity) to the respective proteins of SEQ ID NOS: 2, 4 and 6, and still more preferably at least 95% similarity (still more preferably at least 95% identity) to the respective proteins of SEQ ID NOS: 2, 4 and 6, and also include portions of such proteins with such portion of the protein generally containing at least 30 amino acids and more preferably at least 50 amino acids and most preferably at least up to 150 amino acids, or more. Particularly, preferred portions are immunogenic portions that have very low homology to known proteins of a particular vector or host wherein the proteins would be heterologous.

As known in the art "similarity" between two proteins is determined by comparing the amino acid sequence and its conserved amino acid substitutes of one protein to the sequence of a second protein. The definition of 70% similarity would include a 70 amino acid sequence fragment of a 100 amino acid sequence, for example, or a 70 amino acid sequence obtained by sequentially or randomly deleting 30 amino acids from the 100 amino acid sequence.

The polypeptides corresponding to SEQ ID NOS:2, 4 and 6, respectively, and the polynucleotides encoding them, SEQ ID NOS:1, 3 and 5, display homology to ADE2, LEU2 and HIS3 of the yeast species Saccromyces cervisiae. Accordingly, such polypeptides according to the present invention would be expected to have similar biological activity to their respective Saccromyces cervisiae protein homolog.

A variant, i.e. a "fragment", "analog" or "derivative" polypeptide, and reference polypeptide may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and lie; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the proteins of the present invention may be employed for producing the corresponding full-length protein by peptide synthesis; therefore, the fragments may be employed as intermediates for producing the full-length proteins. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of proteins of the invention by recombinant techniques.

Host cells are genetically engineered (transduced or transformed or transfected) with the vectors of this invention which may be, for example, a cloning vector such as an expression vector. The vector may be, for example, in the form of a plasmid, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing proteins by recombinant techniques. Thus, for example, the polynucleotide may be included in any one of a variety of expression vectors for expressing a protein. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Bacillus subtilis; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II KS, ptrc99a, pKK223-3, pDR540, pRIT2T (Pharmacia); Eukaryotic: pXT1, pSG5 (Stratagene) pSVK3, pBPV, pMSG, pSVL SV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacl, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-l. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., *Basic Methods in Molecular Biology*, (1986)).

The constructs in host cells can be used in a conventional manner to produce the gene product encoded by the recombinant sequence. Alternatively, the proteins of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual, Second Edition*, Cold Spring Harbor, N.Y., (1989), the disclosure of which is hereby incorporated by reference.

Transcription of the DNA encoding the proteins of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, *Cell*, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The proteins according to the invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The proteins of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the proteins of the present invention may be glycosylated or may be non-glycosylated. Proteins of the invention may or may not also include an initial methionine amino acid residue.

Antibodies generated against a protein corresponding to a sequence of the present invention can be obtained by direct injection of the respective protein (or a portion of the protein) into an animal or by administering the proteins to an animal, preferably a nonhuman. The antibody so obtained will then bind the respective protein itself. In this manner, even a sequence encoding only a fragment of the proteins can be used to generate antibodies binding the whole native proteins. Such antibodies can then be used to isolate the protein from cells expressing that protein and may also be useful as antimicrobials, or controls in assays to determine the efficacy of potential antimicrobials.

For preparation of monoclonal antibodies, any technique which provides antibodies produced by continuous cell line cultures can be used. Examples include the hybridoma technique (Kohler and Milstein, *Nature*, 256:495–497, 1975), the trioma technique, the human B-cell hybridoma technique (Kozbor et al., *Immunology Today* 4:72, 1983), and the EBV-hybridoma technique to produce human monoclonal antibodies (Cole et al., in *Monoclonal Antibodies and Cancer Therapy*, Alan R. Liss, Inc., pp. 77–96, 1985).

Techniques described for the production of single chain antibodies (U.S. Pat. No. 4,946,778) can be adapted to produce single chain antibodies to immunogenic protein products of this invention. Also, transgenic mice may be used to express humanized antibodies to immunogenic protein products of this invention.

Antibodies generated against a protein of the present invention may be used in screening for similar proteins from other organisms and samples. Such screening techniques are known in the art, for example, one such screening assay is described in Sambrook and Maniatis, Molecular Cloning: A Laboratory Manual (2d Ed.), vol. 2: Section 8.49, Cold Spring Harbor Laboratory, 1989, which is hereby incorporated by reference in its entirety.

EXAMPLE 1

One-Step Gene Disruption

A mutation is constructed in vitro in a cloned gene and the gene having this mutation is reintroduced into the *Aspergillus fumigatus* wild type microbe. This allows assessment of genetic consequences of a mutation, and may be effectively used to determine whether or not a gene is essential (by determining if a complete gene deletion is viable on non-supplemented or limited supplemental media). The one-step gene disruption technique generates either insertion or deletion mutations.

A one-step gene disruption is generated in *Aspergillus fumigatus* in a single step via transformation, using a fragment of DNA containing a cloned gene that is disrupted by a selectable genetic marker (hygB), i.e., a hisB knock-out construct. A construct is made which corresponds to head and tail portions of the polynucleotide according to SEQ ID NO:1 wherein the center portion has been digested away with restriction enzymes and the marker gene hybB is sandwiched between the head and tail portions. For example, an hygB insert is used having the hygB gene flanked with BamHI and SalI restriction sites. After inverse digestion of the center portion of the polynucleotide sequence according to SEQ ID NO:1 of FIG. 1, the hygB insert is inserted to form the knock-out construct.

Homologous recombination is then carried out between the free DNA ends of the knock-out construct, which are highly recombinogenic, and homologous sequences in the *Aspergillus fumigatus* genome result in replacement of the wild-type gene by the disrupted copy (i.e., by the knockout construct). In this illustration the disrupted gene has a portion deleted and a selectable marker inserted, however the disrupted gene can contain either a simple insertion (of the selectable marker) or a deletion/insertion mutation. Introduction of these disruptions into the genome can be achieved in a single step, resulting in stable, non-reverting mutations.

In the present example, the gene corresponding to SEQ ID NO:1 is mutated to result in a stable, essentially, non-reverting auxotroph of *Aspergillus fumitagus* that requires its growth medium to be supplemented with histidine or its growth and reproduction are significantly affected. In fact, it will eventually die in an in vitro culture which is not supplemented with histidine. The steps utilized are generally as follows.

1. Subclone into gene of interest a suitable selectable gene, creating in the process of subcloning a deletion as well, if desired.
2. Using appropriate restriction sites, excise a linear fragment that contains disrupted gene from plasmid constructed in step 1 and gel purify. Transform with 1 to 10 μg of gel-purified fragment selecting for inserted marker.
   Small amounts of vector sequences can be retained on this fragment without deleterious effects. Ideally, ≧250 bp of the cloned gene should bracket either side of inserted selectable gene, to promote recombination at the chromosomal locus of cloned gene, rather than at site of selectable marker.
3. Confirm structure of disruption by Southern hybridization.

The techniques of the above method are illustrated in FIG. 4. Pure colonies of potential transformant *Aspergillus fumigatus* species are obtained on fully supplemented media. Samples from each of such colonies are screened for histidine auxotrophic properties by utilizing a medium which is fully supplemented except that it lacks histidine. Failure to grow and reproduce on such media (slowed growth and reproduction) indicate a successful transformant histidine auxotroph. Of 175 colonies of potential ransformants screened in a medium lacking the amino acid histidine, 20 ransformant species were identified as auxotrophs of *Aspergillus fumigatus* that require histidine for growth.

Similarly, other auxotrophs lacking the polynucleotide sequence according to SEQ ID NO:1, or another important or essential gene (such as polynucleotides according to SEQ ID NO:2 or SEQ ID NO:3 are produced utilizing the above procedures.

EXAMPLE 2

Use of Histidine Auxotroph to Assay Aspergillus fumigatus cDNA libraries

The histadine auxotroph (or another auxotroph) according to Example 1 above is utilized to screen a cDNA library for the function of such polynucleotide in *Aspergillus fumigatus*.

A cDNA library is formed from *Aspergillus fumigatus* and the cDNA clones are obtained. Preferably, after obtaining the sequence for the cDNA polynucleotide of a particular cDNA clone (for example having a polynucleotide sequence according to SEQ ID NO:2 of FIG. 2), a mutation of the cDNA is constructed in vitro and the gene having this mutation is reintroduced into the *Aspergillus fumigatus* histadine auxotroph. This allows assessment of genetic consequences of such mutation, and may be effectively used to determine whether or not a gene is essential (by determining if a complete gene deletion is viable on non-supplemented or limited supplemental media) and/or to determine its function. The one-step gene disruption technique generating either insertion or deletion mutations is preferred.

A one-step gene disruption is generated in *Aspergillus fumigatus* in a single step via transformation, using a fragment of DNA containing a cloned cDNA gene that is disrupted by a selectable genetic marker construct comprising the polynucleotide sequence according to SEQ ID NO:1), i.e., a cDNA knock-out construct. A construct is made which corresponds to head and tail portions of the polynucleotide as determined for the cDNA wherein the center portion has been digested away with restriction enzymes and the marker gene for histidine according to SEQ ID NO:1 is sandwiched between the head and tail portions. For example, an insert having the polynucleotide sequence according to SEQ ID NO:1 flanked with BamHI and SalI restriction sites. After inverse digestion of the center portion of the polynucleotide sequence of the cDNA, the insert comprising the polynucleotide sequence according to SEQ ID NO:1 is inserted to form the knock-out construct against the cDNA of interest.

Homologous recombination is then carried out between the free DNA ends of the knock-out construct, which are highly recombinogenic, and homologous sequences in the *Aspergillus fumigatus* genome result in replacement of the wild-type gene by the disrupted copy (i.e., by the knockout construct). In this illustration the disrupted gene has a portion deleted and a selectable marker inserted, however the disrupted gene can contain either a simple insertion (of the selectable marker) or a deletion/insertion mutation. Introduction of these disruptions into the genome can be achieved in a single step, resulting in stable, non-reverting mutations.

In the present example, the gene corresponding to the cDNA of interest is mutated to result in a removal of the histidine auxotrophic characteristics of *Aspergillus fumitagus* in that it no longer requires its growth medium to be supplemented with histidine to prevent its growth and reproduction are significantly affected.

Successful transformations are efficiently screened with a media that is fully supplement except that it lacks the amino acid histadine. Species that survive on such media indicate that successful cross-over has occurred and that the cDNA gene has been placed by the knock-out construct that reverses the requirement for histidine supplemented media. Pure colonies of the transformants are obtained of supplemented media and then screened further for other lost properties.

Advantageously, multiple screening plates are utilized from which a single nutrient or factor has been removed. Slowed growth and reproduction or cell death on a media lacking a certain nutrient or factor indicates the function of the cDNA clone polynucleotide. In the instant illustration when the transformants are screened on a media lacking adenylic acid, cell death occurs. Therefore, the polynucleotide according to SEQ ID NO:2 of FIG. 2 encodes a protein critical to the production of adenylic acid in *Aspergillus fumigatus*. Similarly, other cDNA clones from *Aspergillus fumigatus* may be screen for their function with this organism.

As shown by the above example, inter alia the auxotrophs according to the present invention are useful to study cDNA libraries of *Aspergillus fumigatus*.

Numerous modifications and variations of the present invention are possible in light of the above teachings and, therefore, within the scope of the appended claims, the invention may be practiced otherwise than as particularly described.

What is claimed is:

1. An isolated polypeptide comprising an amino acid sequence at least 95% identical to the amino acid sequence selected from the group consisting of:
   (a) amino acids 2 to 244 of SEQ ID NO: 2;
   (b) amino acids 2 to 572 of SEQ ID NO: 4; and
   (c) amino acids 2 to 366 of SEQ ID NO: 6,
wherein when a cell that otherwise expresses said polypeptide is engineered to not express said polypeptide said non-expression renders the cell auxotrophically dependent on producing said polypeptide.

2. An isolated polypeptide comprising an amino acid sequence selected from the group consisting of:
   (a) amino acids 2 to 244 of SEQ ID NO: 2;
   (b) amino acids 2 to 572 of SEQ ID NO: 4; and
   (c) amino acids 2 to 366 of SEQ ID NO: 6.

3. The isolated polypeptide of claim 2 wherein said polypeptide further comprises a leader sequence at the amino terminal portion of said polypeptide.

4. The isolated polypeptide of claim 2 wherein said leader sequence is a signal sequence.

5. The isolated polypeptide of claim 2 wherein said polypeptide further comprises a proprotein sequence.

6. The isolated polypeptide of claim 5 wherein said proprotein sequence is at the amino terminal of said polypeptide.

7. The isolated polypeptide of claim 5 wherein said proprotein sequence is at the carboxyl terminal of said polypeptide.

8. The isolated polypeptide of claim 2 wherein said polypeptide further comprises a secretory sequence.

9. The isolated polypeptide of claim 1 wherein said polypeptide further comprises a leader sequence at the amino terminal portion of said polypeptide.

10. The isolated polypeptide of claim 9 wherein said leader sequence is a signal sequence.

11. The isolated polypeptide of claim 1 wherein said polypeptide further comprises a proprotein sequence.

12. The isolated polypeptide of claim 11 wherein said proprotein sequence is at the amino terminal of said polypeptide.

13. The isolated polypeptide of claim 1 wherein said proprotein sequence is at the carboxyl terminal of said polypeptide.

14. The isolated polypeptide of claim 1 wherein said polypeptide further comprises a secretory sequence.

15. The isolated polypeptide of claim 1 wherein said cell is *Aspergillus fumigatus*.

16. The isolated polypeptide of claim 1 wherein said 95% identical amino acid sequence differs from the sequence of SEQ ID NO: 2, 4 or 6 by a conservative amino acid substitution.

* * * * *

SEQUENCE LISTING

<160> NUMBER OF SEQ ID NOS: 6

<210> SEQ ID NO 1
<211> LENGTH: 732
<212> TYPE: DNA
<213> ORGANISM: Artificial Sequence
<220> FEATURE:
<223> OTHER INFORMATION: Description of Artificial Sequence:cDNA derived
      from Aspergillus fumigatus

<400> SEQUENCE: 1

```
atgtctctcc ccgcacgaac agcgaccgtc tcgcgggtga ccaacgagac caagatccag      60
gtgtctctct ctctcgacgg cggcgtcctc cctccatatg agccgtcaga tcatttccct     120
gctcctgaag acccgaagga ggcagaggcc gccaagcatg gcatcgtccc ccccaaaaat     180
gccgcccatg cgacccagtt cacaccgacc cagcagatca ccgtaagcac ggggatcgga     240
tttctggatc acatgctgca tgctctcgcc aaacactctg ggtggagttt agccatcaga     300
gccaagggag atctgtacat tgacgaccac cacaccaccg aagatacctt ccttgcgctc     360
ggtaccgcct ttaccaaagc tctaggcgcc cggcaatctc ttgcacgatt tggacgcggc     420
gacgctccac tcgacgaggc tctctcctgg gctgtgatcg acctctccag ccgtccctgg     480
gccgtgatca acctgggctt caagcgggag aagatcggag acctgagcac cgagatgatc     540
actcatggac tgcacagctt cgcgcaggct gccgatgtaa cgctgcatgt tggctgcaca     600
tacggagata acgaccacca ccgtgcagag agtgcgttca aggcgctggc cgtagctatc     660
cgcactgcct gtaccagaag ggtggctggc gaagttggag cgggagatgt ggttagtaca     720
aagggagtgc tg                                                         732
```

```
<210> SEQ ID NO 2
<211> LENGTH: 244
<212> TYPE: PRT
<213> ORGANISM: Artificial Sequence
<220> FEATURE:
<223> OTHER INFORMATION: Description of Artificial Sequence:Putative
      protein sequence derived from cDNA of SEQ ID NO:1

<400> SEQUENCE: 2

Met Ser Leu Pro Ala Arg Thr Ala Thr Val Ser Arg Val Thr Asn Glu
 1               5                  10                  15

Thr Lys Ile Gln Val Ser Leu Ser Leu Asp Gly Gly Val Leu Pro Pro
            20                  25                  30

Tyr Glu Pro Ser Asp His Phe Pro Ala Pro Glu Asp Pro Lys Glu Ala
        35                  40                  45

Glu Ala Lys His Gly Ile Val Pro Pro Lys Asn Ala Ala His Ala
    50                  55                  60

Thr Gln Phe Thr Pro Thr Gln Gln Ile Thr Val Ser Thr Gly Ile Gly
65                  70                  75                  80

Phe Leu Asp His Met Leu His Ala Leu Ala Lys His Ser Gly Trp Ser
                85                  90                  95

Leu Ala Ile Arg Ala Lys Gly Asp Leu Tyr Ile Asp Asp His His Thr
            100                 105                 110

Thr Glu Asp Thr Phe Leu Ala Leu Gly Thr Ala Phe Thr Lys Ala Leu
        115                 120                 125

Gly Ala Arg Gln Ser Leu Ala Arg Phe Gly Arg Gly Asp Ala Pro Leu
    130                 135                 140

Asp Glu Ala Leu Ser Trp Ala Val Ile Asp Leu Ser Ser Arg Pro Trp
145                 150                 155                 160

Ala Val Ile Asn Leu Gly Phe Lys Arg Glu Lys Ile Gly Asp Leu Ser
                165                 170                 175

Thr Glu Met Ile Thr His Gly Leu His Ser Phe Ala Gln Ala Ala Asp
            180                 185                 190

Val Thr Leu His Val Gly Cys Thr Tyr Gly Asp Asn Asp His His Arg
        195                 200                 205

Ala Glu Ser Ala Phe Lys Ala Leu Ala Val Ala Ile Arg Thr Ala Cys
    210                 215                 220

Thr Arg Arg Val Ala Gly Glu Val Gly Ala Gly Asp Val Val Ser Thr
225                 230                 235                 240

Lys Gly Val Leu

<210> SEQ ID NO 3
<211> LENGTH: 1716
<212> TYPE: DNA
<213> ORGANISM: Artificial Sequence
<220> FEATURE:
<223> OTHER INFORMATION: Description of Artificial Sequence:cDNA derived
      from Aspergillus fumigatus

<400> SEQUENCE: 3
atgtggaact ctccaaaggt gggggtcctc ggtggaggtc agttgggacg aatgcttgtt     60
gagtcggcga accgacttaa tatccaggtc aatgttctgg acgccggtaa cgcccctgcg    120
aaacaaatta gcgcccacga cggccatgtg actggctcat tcaaggatcg tgaagctgtg    180
cggacgttgg cgaggacctg cgacgttgtg acgccgaga tcgagcatgt tgatacatac     240
gctcttgagg agatctccgc ggaggtcaag gttgagccca gctggcaagc gatccgaaca    300
atccagaaca agttcaatca gaaggaacac cttcggaaat atggcatacc aatggcggag    360
```

-continued

```
caccgggagc tgcttgagaa cacgccggct gaactcgccc agatcggcga acagcttggg    420
tatcccttga tgctcaagtc gaagacgatg gcctacgacg gacggggaaa cttccgtgtc    480
aattccaagg acgatatccc cgaagcgctt gaagcgctca aggaccggcc attgtacgct    540
gagaaatggg cctacttcaa gatggaattg gccgtaatgg ttgtgaaaac caaggacgcg    600
gtcctctcat accccacagt cgagacagta caagaagatt cgatatgcaa gctcgtctac    660
gcacctgccc gcaatgtctc cgacgccatc aaccagaaag cccaggagct agcccgcaag    720
gctgtcgcag ccttttgacgg caagggtgct ttcggtgtgg agatgttcct tctcgaggac    780
gacagcatca tgctgtgcga aattgccagc cgcatccaca actcgggcca ctacacaatt    840
gaaggttgta ccctgtccca atttgacgcc cacctacgtg ccattctcga cctccccatt    900
cccctcaga gcctcgaaat ccgccaaccg tccatcatgc tcaacatcat ggcggcgcc    960
gccccagaca cccacctgaa agccgccgag gccgctctct ccatcCCcaa cgccagcatt   1020
cacctctaca gcaagggcgc cgccaagccc ggccgcaaga tgggccacgt caccgttacc   1080
gcgtccacga tgcacgaagc cgagaaatac atccagcccc tgatcgacgt tgttgacgag   1140
atccgctcga agcgcagcga catcaagaca cagcccgtca agtccggccc gtcgaagccc   1200
gcccccaccg ttgctgtgat gatgggctcc gatagcgacc tcaagacact cgttccgggc   1260
ctgaaactcc tccgtgacta cttcggcatc gagcccgccg tcgacatcac ctccgcccat   1320
cgcaccccaa cgttcatggc cgagtactca gccagcgcag ccgcgcgcgg cattaaggtc   1380
attatcgccg ctgcgggcgg cgccgcccat ctccctggga tggctgccgc acacaccgtc   1440
ctgcccgtca tcggcgtacc ggtcaagggc agctcgctag acggcgtgga cagcctgtac   1500
agcatcgtcc agatgcctag aggtgttccc gtcgcgacgg taggaatcaa caacagcatc   1560
aacgctgccc tcctggcagc tcgtatcctt ggcacattcg acccggctat ccagcgtaag   1620
gtggaggcgt atgccgagca ggctagacac gagaacatgg agttgaaggg gaccaagatg   1680
caggaactcg gatgggaaaa gtactttgaa cagatg                              1716
```

<210> SEQ ID NO 4
<211> LENGTH: 572
<212> TYPE: PRT
<213> ORGANISM: Artificial Sequence
<220> FEATURE:
<223> OTHER INFORMATION: Description of Artificial Sequence:Putative
      protein sequence derived from cDNA of SEQ ID NO:3

<400> SEQUENCE: 4

```
Met Trp Asn Ser Pro Lys Val Gly Val Leu Gly Gly Gln Leu Gly
 1               5                  10                  15

Arg Met Leu Val Glu Ser Ala Asn Arg Leu Asn Ile Gln Val Asn Val
                20                  25                  30

Leu Asp Ala Gly Asn Ala Pro Ala Lys Gln Ile Ser Ala His Asp Gly
            35                  40                  45

His Val Thr Gly Ser Phe Lys Asp Arg Glu Ala Val Arg Thr Leu Ala
        50                  55                  60

Arg Thr Cys Asp Val Val Thr Ala Glu Ile Glu His Val Asp Thr Tyr
    65                  70                  75                  80

Ala Leu Glu Glu Ile Ser Ala Glu Val Lys Val Glu Pro Ser Trp Gln
                85                  90                  95

Ala Ile Arg Thr Ile Gln Asn Lys Phe Asn Gln Lys Glu His Leu Arg
            100                 105                 110
```

-continued

Lys Tyr Gly Ile Pro Met Ala Glu His Arg Glu Leu Leu Glu Asn Thr
        115                 120                 125

Pro Ala Glu Leu Ala Gln Ile Gly Glu Gln Leu Gly Tyr Pro Leu Met
        130                 135                 140

Leu Lys Ser Lys Thr Met Ala Tyr Asp Gly Arg Gly Asn Phe Arg Val
145                 150                 155                 160

Asn Ser Lys Asp Asp Ile Pro Glu Ala Leu Glu Ala Leu Lys Asp Arg
                165                 170                 175

Pro Leu Tyr Ala Glu Lys Trp Ala Tyr Phe Lys Met Glu Leu Ala Val
        180                 185                 190

Met Val Val Lys Thr Lys Asp Ala Val Leu Ser Tyr Pro Thr Val Glu
        195                 200                 205

Thr Val Gln Glu Asp Ser Ile Cys Lys Leu Val Tyr Ala Pro Ala Arg
        210                 215                 220

Asn Val Ser Asp Ala Ile Asn Gln Lys Ala Gln Glu Leu Ala Arg Lys
225                 230                 235                 240

Ala Val Ala Ala Phe Asp Gly Lys Gly Ala Phe Gly Val Glu Met Phe
                245                 250                 255

Leu Leu Glu Asp Asp Ser Ile Met Leu Cys Glu Ile Ala Ser Arg Ile
        260                 265                 270

His Asn Ser Gly His Tyr Thr Ile Glu Gly Cys Thr Leu Ser Gln Phe
        275                 280                 285

Asp Ala His Leu Arg Ala Ile Leu Asp Leu Pro Ile Pro Pro Gln Ser
        290                 295                 300

Leu Glu Ile Arg Gln Pro Ser Ile Met Leu Asn Ile Ile Gly Gly Ala
305                 310                 315                 320

Ala Pro Asp Thr His Leu Lys Ala Ala Glu Ala Ala Leu Ser Ile Pro
                325                 330                 335

Asn Ala Ser Ile His Leu Tyr Ser Lys Gly Ala Lys Pro Gly Arg
        340                 345                 350

Lys Met Gly His Val Thr Val Thr Ala Ser Thr Met His Glu Ala Glu
        355                 360                 365

Lys Tyr Ile Gln Pro Leu Ile Asp Val Val Asp Glu Ile Arg Ser Lys
        370                 375                 380

Arg Ser Asp Ile Lys Thr Gln Pro Val Lys Ser Gly Pro Ser Lys Pro
385                 390                 395                 400

Ala Pro Thr Val Ala Val Met Met Gly Ser Asp Ser Asp Leu Lys Thr
                405                 410                 415

Leu Val Pro Gly Leu Lys Leu Leu Arg Asp Tyr Phe Gly Ile Glu Pro
        420                 425                 430

Ala Val Asp Ile Thr Ser Ala His Arg Thr Pro Thr Phe Met Ala Glu
        435                 440                 445

Tyr Ser Ala Ser Ala Ala Arg Gly Ile Lys Val Ile Ile Ala Ala
        450                 455                 460

Ala Gly Gly Ala Ala His Leu Pro Gly Met Ala Ala His Thr Val
465                 470                 475                 480

Leu Pro Val Ile Gly Val Pro Val Lys Gly Ser Ser Leu Asp Gly Val
                485                 490                 495

Asp Ser Leu Tyr Ser Ile Val Gln Met Pro Arg Gly Val Pro Val Ala
        500                 505                 510

Thr Val Gly Ile Asn Asn Ser Ile Asn Ala Ala Leu Leu Ala Ala Arg
        515                 520                 525

Ile Leu Gly Thr Phe Asp Pro Ala Ile Gln Arg Lys Val Glu Ala Tyr

```
                530             535             540
Ala Glu Gln Ala Arg His Glu Asn Met Glu Leu Lys Gly Thr Lys Met
545                 550                 555                 560

Gln Glu Leu Gly Trp Glu Lys Tyr Phe Glu Gln Met
                565                 570

<210> SEQ ID NO 5
<211> LENGTH: 1098
<212> TYPE: DNA
<213> ORGANISM: Artificial Sequence
<220> FEATURE:
<223> OTHER INFORMATION: Description of Artificial Sequence:cDNA derived
      from Aspergillus fumigatus

<400> SEQUENCE: 5
atgccgtcat ataacattgt cgttttcgct ggggaccact gtggtccgga ggtgaccgct     60
gaggcaatca aggtcctgcg cgtcatcgag aagtgccgtg acgatgctac cttcaacctc    120
caggatcaat tgctcggtgg tgcatcgatc gatgctaccg gatctcccct taccgacgaa    180
gctcttaacg ccgcaaagaa cgccgatgcc gttctcctcg gtgccattgg cggtcccaaa    240
tggggcactg gcgccgtccg ccccgaacag ggcctcctcc gtctgcgcaa ggagatgggc    300
acattcggta acctccgccc ctgcaacttc gccgccccgt cgctggtcga cggctcccct    360
ctccgccccg aagtctgccg cggcgtcgac ttcaacatta tccgcgaact gaccggtggc    420
atctacttcg cgaccgcaa ggaggacgac ggcagcggct cgccatgga cacggagccg    480 tactcccgcg cggagatcga gcgcatcacc cgccttgcgg cccacctcgc tctgcagcac    540 aaccccctc ttcccgtgtg gagcttggac aaggccaacg tcctcgcgac gagccggctg    600
tggcggaaga ccgtgacgga ggtcatggcc aaggagttcc cccagctcaa ggtggagcac    660
cagctcattg actccgcggc catgatcatg gtcaaggagc ctagaaagct taacggtatt    720
gttgtcacta gcaacctgtt cggtgacatc atcagtgatg aagccagcgt tatccctggt    780
tctctgggac tcttgcccag cgcaagcttg agcggcattc ctgacggaaa gaccaaggtc    840
aatggtatct atgagcctat tcacggttct gcccctgaca ttgccggcaa gggcatcgtt    900
aaccccgtcg ccgccattct ctctgtcgcc atgatgatgc agtactccct gaaccgtatg    960
gatgacgcca gggccatcga cacggccgtc cgcaatgtga tcgaggccgg tatccgcact   1020
gccgatattg gcggcaagtc gacaactagc gaggtcggtg acgctgttgc tgccgagctg   1080
gagaagctgt tgaagcaa                                                 1098

<210> SEQ ID NO 6
<211> LENGTH: 366
<212> TYPE: PRT
<213> ORGANISM: Artificial Sequence
<220> FEATURE:
<223> OTHER INFORMATION: Description of Artificial Sequence:Putative
      protein sequence derived from cDNA of SEQ ID NO:5

<400> SEQUENCE: 6

Met Pro Ser Tyr Asn Ile Val Val Phe Ala Gly Asp His Cys Gly Pro
 1               5                  10                  15

Glu Val Thr Ala Glu Ala Ile Lys Val Leu Arg Val Ile Glu Lys Cys
            20                  25                  30

Arg Asp Asp Ala Thr Phe Asn Leu Gln Asp Gln Leu Leu Gly Gly Ala
        35                  40                  45

Ser Ile Asp Ala Thr Gly Ser Pro Leu Thr Asp Glu Ala Leu Asn Ala
    50                  55                  60
```

```
Ala Lys Asn Ala Asp Ala Val Leu Leu Gly Ala Ile Gly Gly Pro Lys
 65                  70                  75                  80

Trp Gly Thr Gly Ala Val Arg Pro Glu Gln Gly Leu Leu Arg Leu Arg
             85                  90                  95

Lys Glu Met Gly Thr Phe Gly Asn Leu Arg Pro Cys Asn Phe Ala Ala
            100                 105                 110

Pro Ser Leu Val Asp Gly Ser Pro Leu Arg Pro Glu Val Cys Arg Gly
        115                 120                 125

Val Asp Phe Asn Ile Ile Arg Glu Leu Thr Gly Gly Ile Tyr Phe Gly
        130                 135                 140

Asp Arg Lys Glu Asp Gly Ser Gly Phe Ala Met Asp Thr Glu Pro
145                 150                 155                 160

Tyr Ser Arg Ala Glu Ile Glu Arg Ile Thr Arg Leu Ala Ala His Leu
            165                 170                 175

Ala Leu Gln His Asn Pro Pro Leu Pro Val Trp Ser Leu Asp Lys Ala
            180                 185                 190

Asn Val Leu Ala Thr Ser Arg Leu Trp Arg Lys Thr Val Thr Glu Val
        195                 200                 205

Met Ala Lys Glu Phe Pro Gln Leu Lys Val Glu His Gln Leu Ile Asp
        210                 215                 220

Ser Ala Ala Met Ile Met Val Lys Glu Pro Arg Lys Leu Asn Gly Ile
225                 230                 235                 240

Val Val Thr Ser Asn Leu Phe Gly Asp Ile Ile Ser Asp Glu Ala Ser
            245                 250                 255

Val Ile Pro Gly Ser Leu Gly Leu Leu Pro Ser Ala Ser Leu Ser Gly
            260                 265                 270

Ile Pro Asp Gly Lys Thr Lys Val Asn Gly Ile Tyr Glu Pro Ile His
        275                 280                 285

Gly Ser Ala Pro Asp Ile Ala Gly Lys Gly Ile Val Asn Pro Val Ala
        290                 295                 300

Ala Ile Leu Ser Val Ala Met Met Met Gln Tyr Ser Leu Asn Arg Met
305                 310                 315                 320

Asp Asp Ala Arg Ala Ile Glu Thr Ala Val Arg Asn Val Ile Glu Ala
            325                 330                 335

Gly Ile Arg Thr Ala Asp Ile Gly Gly Lys Ser Thr Thr Ser Glu Val
            340                 345                 350

Gly Asp Ala Val Ala Ala Glu Leu Glu Lys Leu Leu Lys Gln
        355                 360                 365
```